United States Patent
Wang et al.

(10) Patent No.: US 7,820,587 B2
(45) Date of Patent: Oct. 26, 2010

(54) POROUS ANODIC ALUMINUM OXIDE MEMBRANES FOR NANOFABRICATION

(75) Inventors: Hsien-Hau Wang, Downers Grove, IL (US); Jianjiang Lu, Houston, TX (US); Shufang Yu, Orefield, PA (US)

(73) Assignee: UChicago Argonne, LLC, Chicago, IL (US)

( * ) Notice: Subject to any disclaimer, the term of this patent is extended or adjusted under 35 U.S.C. 154(b) by 823 days.

(21) Appl. No.: 11/606,310

(22) Filed: Nov. 28, 2006

(65) Prior Publication Data

US 2007/0151850 A1    Jul. 5, 2007

Related U.S. Application Data

(60) Provisional application No. 60/740,467, filed on Nov. 28, 2005.

(51) Int. Cl.
   *B01J 23/44*    (2006.01)
(52) U.S. Cl. ........................... 502/325; 502/326
(58) Field of Classification Search .................. 502/325, 502/339, 334, 326; 204/406, 412; 205/429
   See application file for complete search history.

(56) References Cited

U.S. PATENT DOCUMENTS 4,844,788 A * 7/1989 Takahashi et al. ........... 204/406

6,919,294 B2 * 7/2005 Saito et al. .................. 502/305

OTHER PUBLICATIONS

C. Chrisofides and S. Mandelis, J. Appl. Phys. 68 (6) R1 (Sep. 1990).
J. Bodzenta, B. Burak, Z. Gacek, et al.. Sensors and Acuators B 87, 82-87 (2002).
F. Favier, E.C. Walter et al, Science vol. 293, 2227-2231 (Sep. 2001).
T. Xu and M.P. Zach et al. Appl. Phys. Lett. 86, 203104 (2005).
J. Kong, M.G. Chaplin, H. Dai, Adv. Mater.13 No. 18 1384-1386 (Sep. 2001).
G.E. Thompson and G.C. Wood, Nature vol. 290, 230-232 (Mar. 1981).
M. Steinhart et al. Adv. Mater. 15, No. 9, 706-709, (May 2003).
S. Yu, U. Welp, L.Z. Hua et al. Chem. Mater. 17, 3445-3450 (2005).
G.W. Crabtree, M.S. Dresselhaus and M.V. Buchanan, Physics Today vol. 12, 39-44 (Dec. 2004).

* cited by examiner

*Primary Examiner*—Timothy C Vanoy
*Assistant Examiner*—Michelle Hou
(74) *Attorney, Agent, or Firm*—Olson & Cepuritis, Ltd.

(57) ABSTRACT

A hydrogen detector with a porous layer of alumina. Pores with average pore diameters in the range of from about 10 to about 200 nanometers (nms) and average pore depths in the range of from about 10 to about 1000 nms have Pd nanoparticles in the pores forming a film. Electrodes on the Pd film measure changes in electrical resistance of the Pd film in the presence of hydrogen. Pd may be in the form of nanotubes. The alumina is anodized for various times to form the nanowalls or pores and vary the pore depths.

20 Claims, 6 Drawing Sheets

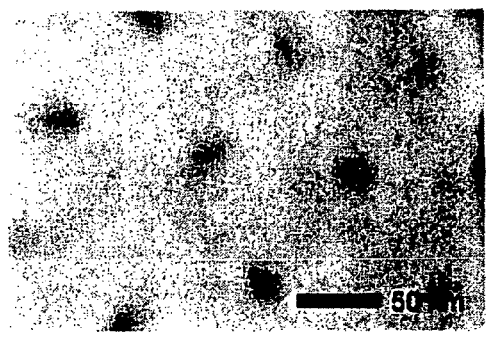
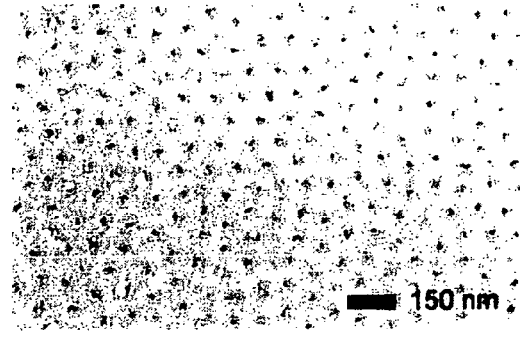
FIG. 1(a)
FIG. 1(b)

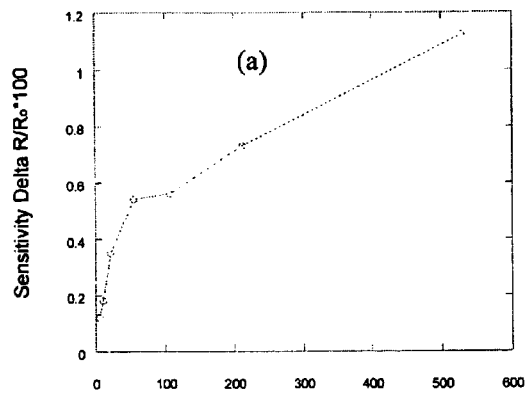
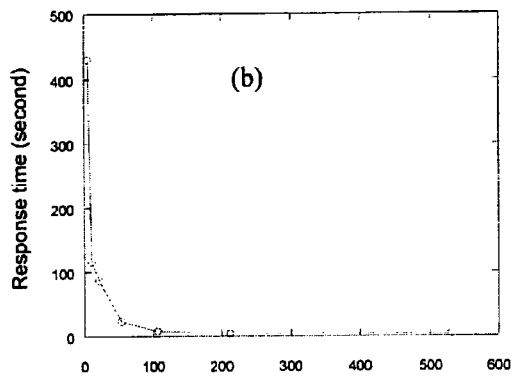
FIG. 6(a)   FIG. 6(b)
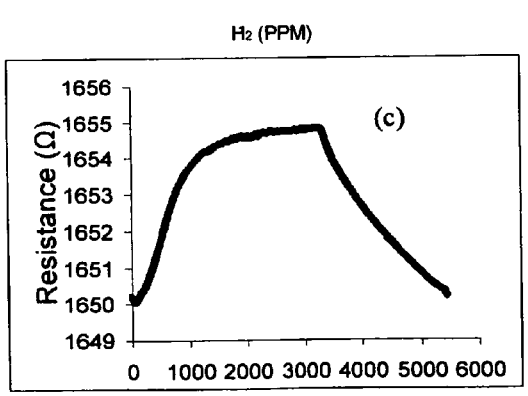
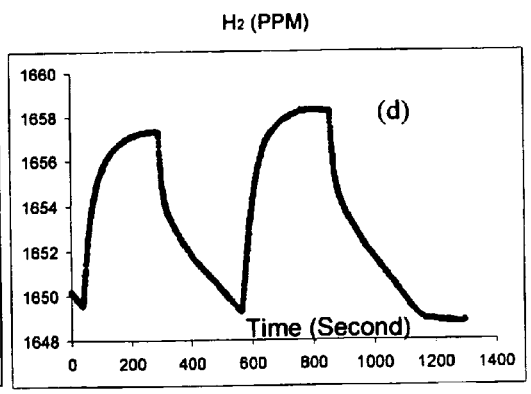
FIG. 6(c)   FIG. 6(d)

POROUS ANODIC ALUMINUM OXIDE MEMBRANES FOR NANOFABRICATION

RELATED APPLICATIONS

This application claims the benefit under Title 35, United States Code §119(e) of U.S. provisional application Ser. No. 60/740,467 filed Nov. 28, 2005.

CONTRACTUAL ORIGIN OF THE INVENTION

The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

BACKGROUND OF THE INVENTION

Hydrogen is an extremely clean energy source for use in fuel cells and internal combustion engines. However, widespread use of hydrogen as a fuel will require innovations in hydrogen storage and hydrogen sensing. Reliable, cheap, compact, and safe hydrogen sensors are needed both for measuring the hydrogen concentration in flowing gas streams and for monitoring ambient air for leaked hydrogen. It is essential that "alarm" sensors detect hydrogen at a concentration well below the lower explosion limit in air of 4%.

Currently, commercial hydrogen sensors suffer from their lengthy response time and high cost. In addition, the working temperatures are usually high. Therefore, explorations for new methods that lead to inexpensive, convenient and fast response hydrogen sensors are crucial for the future application of hydrogen fuel. Palladium metal has long been recognized as the desired material for hydrogen sensing. In principle, Pd metal swells upon exposure to hydrogen gas that results in resistance change. Recent advances in the synthesis of Pd nanostructure based hydrogen sensors lead to a series of new results. Prior art shows that Pd nanostructure based hydrogen sensors are promising due to a decrease in response time. In particular, Pd nanoparticle based hydrogen sensors respond to hydrogen gas in milliseconds. The difficulty is finding an appropriate carrier that can load palladium nanoparticles and functions as a sensor.

Anodized aluminum oxide (AAO) membranes consist of highly uniform and aligned nanopores (hexagonal close packed) with the pore diameter ranging between 10 and 200 nanometers (nms). AAO nanowell structure can be synthesized through short-term anodization of aluminum metal. We found that the thin AAO nanowell structure is an excellent substrate for hydrogen sensing because not only does it provide a rough surface with large surface areas which is a perfect medium for supporting Pd nanostructures but also the surfaces are weakly conductive for better electronic measurements. AAO nanowell hydrogen sensors coated with Pd nanostructures can be achieved either by thermal evaporation or chemical coating Pd metal on an AAO nanowell surface.

SUMMARY OF THE INVENTION

Accordingly, it is a principle object of the present invention to provide a hydrogen detector wherein highly uniform and aligned nanopores have palladium nanoparticles deposited therein providing a new and highly useful hydrogen detector.

Another object of the invention is to provide a hydrogen detector comprising a substrate with a porous layer of alumina, the porous layer having pores therein with average pore diameters in the range of from about 10 to about 200 nanometers (nms) and average pore depths in the range of from about 10 to about 1000 nms, Pd nanoparticles in at least most of the pores forming a film on the alumina porous layer, and electrodes in electrical contact with the Pd film for measuring changes in electrical resistance of the Pd film in the presence of hydrogen.

Another object of the present invention is to provide a hydrogen detector comprising a substrate with a layer of alumina having pores therein oriented in a hexagonally close packed configuration, the pores having average pore diameters in the range of from about 10 to about 200 nanometers (nms) and average pore depths in the range of from about 50 to about 1000 nms with said average pore depth being at least five times the average pore diameter, Pd nanotubes in at least most of the pores forming a film on the alumina layer, and at least two electrodes in electrical contact with the Pd film for measuring changes in electrical resistance of the Pd film in the presence of hydrogen.

A final object of the invention is to provide a method of providing a layered combination useful in detecting the presence of hydrogen, comprising the steps of: (a) providing an aluminum substrate having nanoindents on at least one surface thereof, (b) anodizing the surface having the nanoindents therein for a time sufficient to form pores having average diameters in the range of from about 10 to about 200 nms and average pore depths in the range of from about 10 to about 1000 nms, and (c) providing Pd nanoparticles in at least most of the pores forming a Pd film on the anodized surface.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 1a is a scanning electron microscope (SEM) image of AAO nanowell after 2 minutes anodization before Pd coating;

FIG. 1b is a scanning electron microscope (SEM) image of AAO nanowell after 2 minutes anodization after Pd coating;

FIG. 6a is a graphical representation of sensitivity as a function of hydrogen concentrations using a Pd/AAO-8 minute sensor;

FIG. 6b is a graphical representation of the relationship between response time and hydrogen concentration for a Pd/AAO-8 minute sensor;

FIG. 6c is a graphical representation of the relationship between the resistance in ohms versus time in seconds at a hydrogen concentration of 5 ppm; and FIG. 6d is a graphical representation of the resistance in ohms and time for a hydrogen concentration of 50 ppm.

Figure 2:
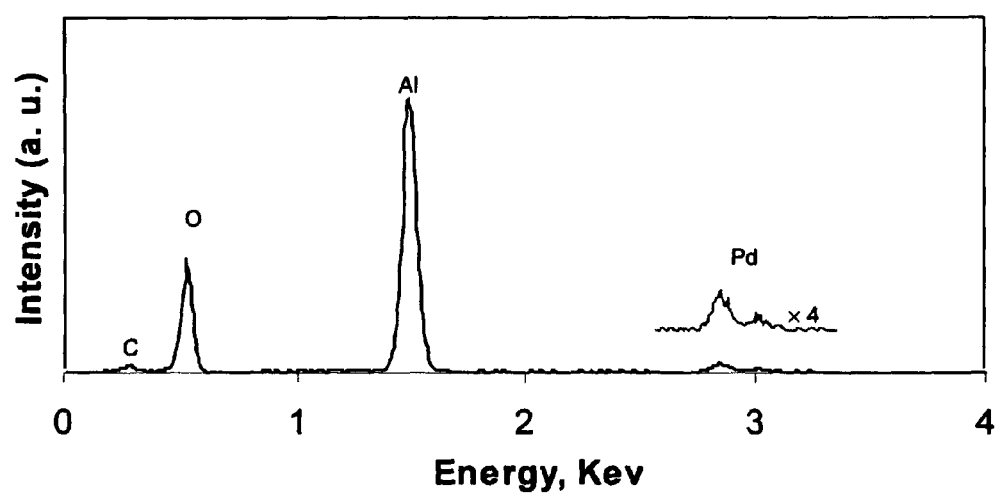
FIG. 2 is a graphic representation of a typical Energy Dispersive X-ray (EDX) spectrum of Pd/AAO nanowell taken from a film as shown in FIG. 1b.

While the invention has been particularly shown and described with reference to a preferred embodiment hereof, it will be understood by those skilled in the art that several changes in form and detail may be made without departing from the spirit and scope of the invention.

DESCRIPTION OF THE PREFERRED EMBODIMENT

AAO nanowells were prepared from high purity aluminum sheets (99.998%, Alfa Aesar) through anodization in an aqueous solution of 0.3 M oxalic acid. Typically, a cleaned aluminum sheet was electro-polished and first anodized in oxalic acid solution for several hours. After removing the initial oxide layer, the second anodization was processed for a short period of time between 0 and 8 min (0 min means no second anodization).

Pd nanostructures were coated on AAO nanowell substrate by following the method reported in M. Stinhart, et al., *Adv. Mater.* 15, 706, (2003), incorporated herein by reference. Briefly, $Pd(OAc)_2$ (0.125 g) and Poly(DL-lactide) (PDLLA, 0.125 g) was first dissolved in 10 mL chloroform to give a red solution. The solution was then used to wet the nanowell surface (0.400 mL over AAO nanowell substrate with a size about 1 $cm^2$). The coated samples were then placed in an oven and heated at 200° C. for 8-14 hours. The palladium coated top surface of AAO nanowell was used as sensing material. The same method was applied to a glass surface and Al surface for comparison.

Field-emission scanning electron microscopy images (FESEM) and energy-dispersive X-ray (EDX) measurements were obtained on a Hitachi S-4700-II filed emission scanning electron microscope operating with an accelerating voltage of 10 KV.

The apparatus used for $H_2$ sensing tests have been disclosed in S. Yu, U. Welp, L. Z. Hua, L. A. Rydh, W. K. Kwok, and H. H. Wang, *Chem. Mater.* 17, 3445, (2005), incorporated herein. The same procedures were used to test the hydrogen sensing ability of other Pd/AAO nanowell sensors disclosed herein. Hydrogen sensing tests were performed on Pd/glass surface, Pd/Al surface as references and 0, 2, 3 and 8 min Pd/AAO nanowell structures. All tests were conducted at room temperature with $H_2$ concentration in the range of 5 ppm to 1%.

AAO nanowell substrates were fabricated by the two-step anodization process. First, aluminum foil was anodized in oxalic acid solution for several hours to generate a porous structure containing nanoindents in hexagonal close packed configuration. The resultant alumina layer from the first anodization was removed by immersing AAO/Al in a solution of chromic acid and phosphorus acid to create a clean aluminum surface with nanoindents. The second anodization was then carried out in the same oxalic acid solution for a short period of time (between 0 and 8 min) to generate a new thin layer of AAO hexagonal pattern on aluminum surface.

SEM images of typical AAO nanowell substrates are shown in FIG. 1. The nanowell structure is made of shallow wells that were oriented in a hexagonally closed packed configuration with average well diameter around 50 nm and average depth generally less than 100 nm. However, nanowells or pores can have average diameters in the range of from about 30 to about 200 nms, with diameters between about 30 to 100 preferred. The nanowell or pore average depth may be in the range of from about 10 to about 1000 nms with average depths generally at least 5 times the average diameters or between about 150 to about 500 nms being preferred. When the average pore depth is at least about 5 times greater than the average pore diameter, then nanotubes are formed as opposed to nanoparticles with use of appropriate transition metal catalysts.

The as-prepared AAO nanowell substrates were then wetted by a $Pd(OAc)_2$ and PDLLA in chloroform solution and calcined under 200° C. in air. After calcination, Pd salt was transformed into Pd nanoparticles with dimension between 10 and 50 nm as shown in FIG. 1b. EDX spectrum in FIG. 2 clearly shows Pd signals at 2.838 Kev (PdLa) and 3.010 Kev (PdLb) which support the presence of Pd element on AAO nanowell substrates. Aluminum and oxygen signals are also found in the same spectrum due to the alumina surface. A carbon signal may come from trace amount of polymer on surface and the chamber environment.

Figure 3:
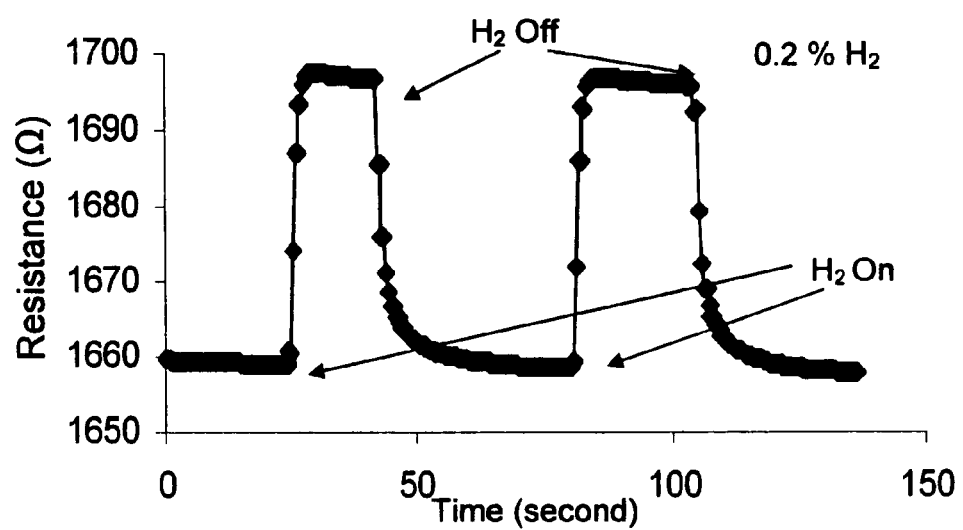
FIG. 3 is a graph showing the relationship between resistance and time for a Pd/AAO-8 minute nanowell hydrogen sensing performance (resistance in ohms verse time, second) with 0.2% $H_2$ in Ar.

A piece of Pd coated AAO nanowell film with the size of 0.3×0.5 $cm^2$ was selected for testing. Two Au wires were attached on the surface near ends of the sensor film. Electrical resistance across the two connected Au wires on each sample was measured with different hydrogen concentration ON and OFF. Pure argon gas and 4% hydrogen in argon were used to create a variety of hydrogen concentrations. The sensors were first stabilized with pure argon gas. Then the sensors were repeatedly exposed to hydrogen gas and pure Ar gas. The resistance changes with time were recorded with use of a computer based data acquisition system, as is well known within the skill of the art. A typical histogram is shown in FIG. 3.

Sensitivity and response time are used here to compare the hydrogen sensing performance of the samples. The sensitivity S is defined as the percentage of resistance change by the formula $$S=(Rs-Ro)/Ro\times 100\%=\Delta R/Ro\times 100\%$$

Figure 4:
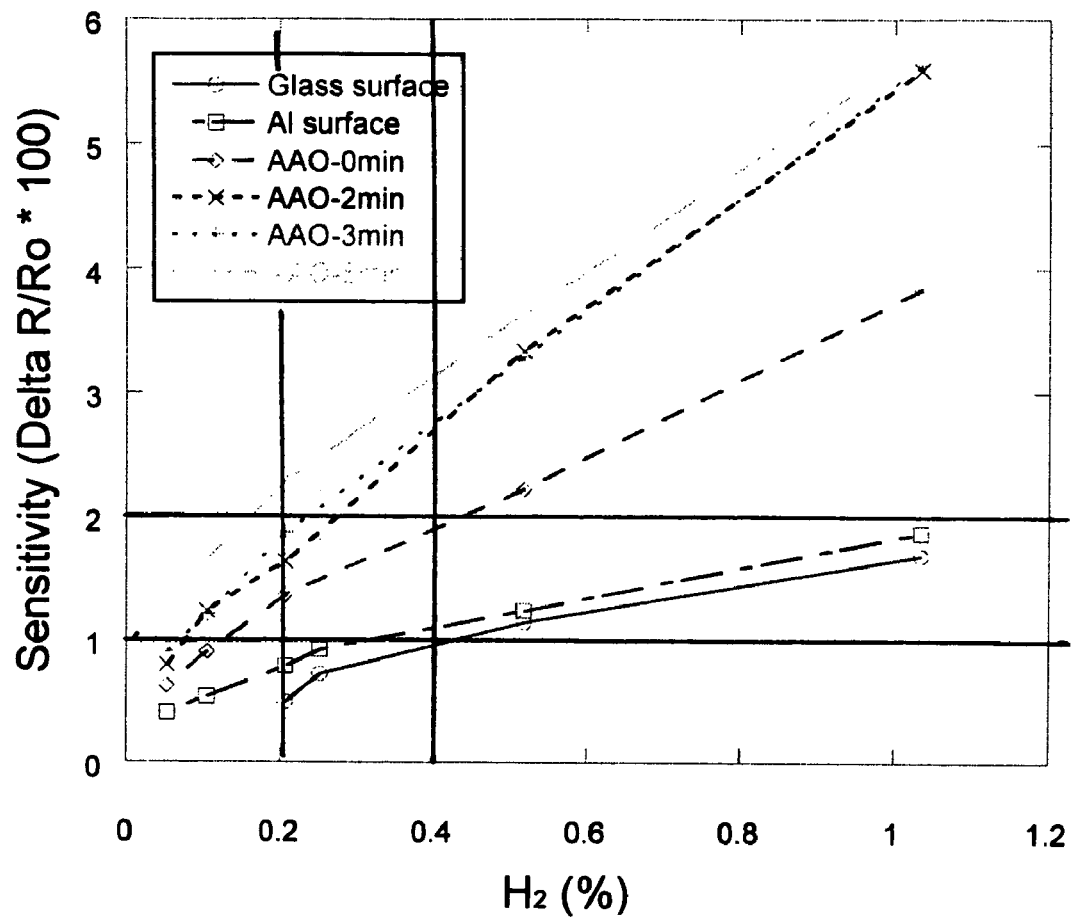
FIG. 4 is a graph showing the relationship between sensitivity and hydrogen concentration for five different sensors.

The response time is defined as the time needed for the sensor to reach $e^{-1}$ or 36.8% of the total change for a given hydrogen concentration. The sensitivities of all six samples as a function of hydrogen concentrations are shown in FIG. 4.

Figure 5:
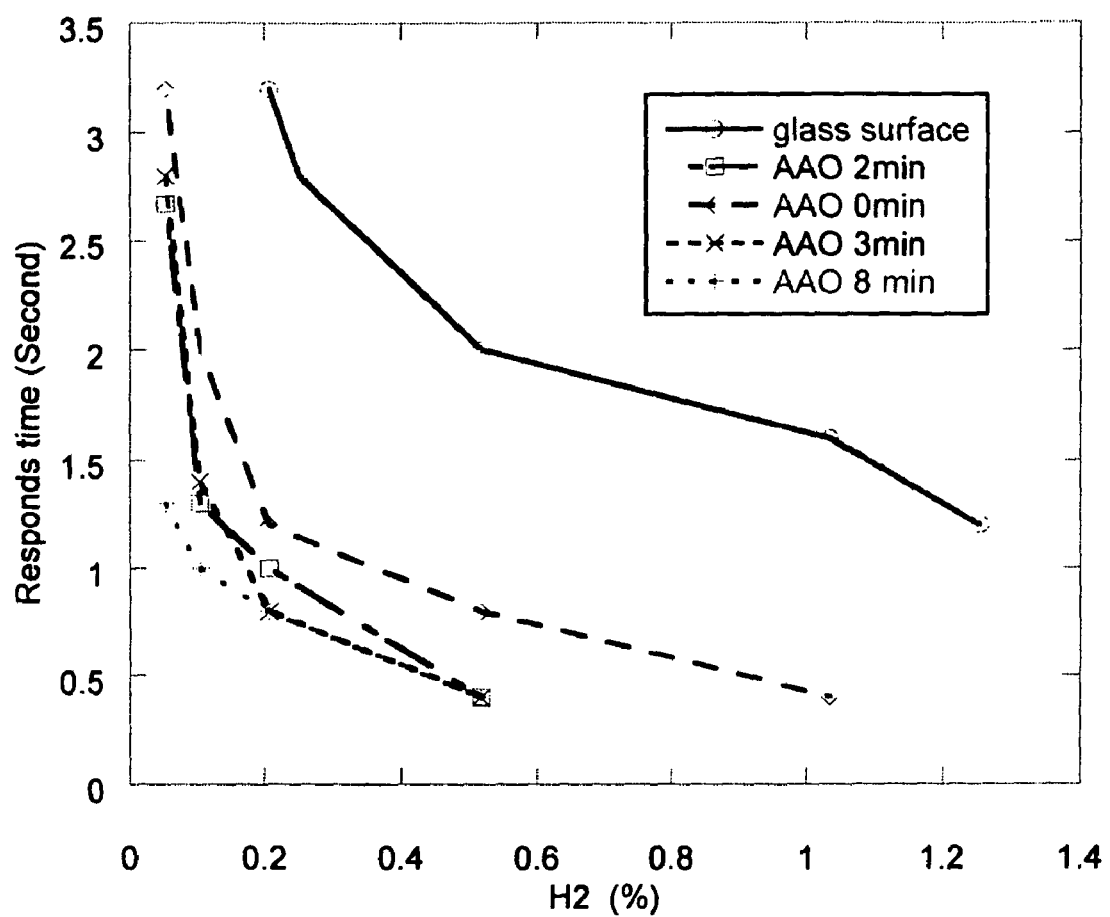
FIG. 5 is a graphical representation of the relationship between the response time and hydrogen concentration for six different sensors.

The results clearly show that in the hydrogen concentration between 0.05% and 1.00%, Pd nanoparticle sensors performed better on AAO substrates than on a glass substrate or an Al surface. The AAO nanowell sensors with 2-8 min anodization time during a second anodization performed better than those without a second anodization (AAO-0 min). For example, when the hydrogen concentration was 1.00%, the sensitivity of Pd/AAO-2, 3, 8 min sensors were about 6 times better than the Pd/glass substrate and about two times better than the Pd/AAO-0 min. All three AAO nanowell sensors with a second anodization have comparable sensitivities. Nevertheless, Pd/AAO-8 min preformed slightly better than the other two sensors. The response time versus hydrogen concentration is shown in FIG. 5. The results show that Pd nanostructure sensors responded faster on AAO nanowell substrates than on a glass surface. These Pd/AAO-nanowell hydrogen sensors are very fast in responding to hydrogen gas at concentrations between 0.05% and 1.00%. Typically, they only require less than one second to reach a resistance change as shown in FIG. 5 at a hydrogen concentration higher than 0.20% (2000 ppm).

Another factor of the increase in second anodization time is the increase in surface roughness of the Pd nanoparticles from a root mean square (RMS) roughness of about 2.5 to about 3.5 for zero minute second anodization to about 10 nm for 2 minute second anodization. The increase in nanowell roughness translates to the Pd film.

Low concentration (5-500 ppm) hydrogen sensing tests were carried out on an AAO-8 min nanowell sensor only as shown in FIGS. 6a and 6b, which show the sensitivity and response time versus hydrogen concentration, respectively. FIGS. 6c and 6d demonstrate two set of sensing data with hydrogen concentrations at 5 ppm and 50 ppm, respectively. At low hydrogen concentration, the sensor responds to hydrogen gas with a much longer time compared to high hydrogen concentrations. For example, about one thousand seconds and one hundred seconds are required to reach resistance change when the hydrogen concentration is 5 ppm and 50 ppm, respectively. However, less than 10 seconds is required when the hydrogen concentration is 500 ppm.

The inventive Pd/AAO nanowell hydrogen sensors show rapid response to hydrogen gas at concentrations between 0.05% and 1%. This fast response is due to the effective dispersing of a thin layer of Pd nanoparticles over AAO nanowell surfaces. PDLLA polymer is an important ingredient for controlling the size distribution of Pd nanoparticles on sensor surface. When the sample was treated similarly but without the polymer, no hydrogen sensing behavior was detected. This may be due to the strong aggregation of the palladium salt. Pd particle sizes here are between 10 and 50 nm according to SEM images (FIG. 1b). Typically, on average, the Pd nanoparticles are about 10 nm wide and about 2 nm thick. The nanoparticles quickly respond to hydrogen gas because, it is believed, they only need a very short time for the hydrogen gas to diffuse into the small volume of individual nanoparticles and reach equilibrium. Since Pd particles respond to hydrogen simultaneously, the fast sensing activity essentially reflects in the whole sensor response. As used herein, nanowells are the same as pores, and Pd nanoparticles are classified as nanotubes when the average depth is at least 5 times greater than the average diameter.

Two different types of substrates were used for comparison, a non-conductive substrate—glass surface, and conductive substrates—Al metal and AAO nanowell (porous) surfaces. For the glass surface, a continuous layer of Pd particles had to be formed for resistance measurements. This process left a thick layer and possible large Pd aggregates and resulted in poor sensing behavior in both sensitivity and slow response time. For the conductive surface, there is no need for a continuous coating. It is because these nanoparticles are effectively bonded to the surface, they function as parallel resistors. The surface conductivities play a significant role on the sensitivity. When the surface is highly conductive as an example shown on the Pd/Al surface (FIG. 4), the sensitivity is low due to the shunt effect of the Al surface. When the electrical resistance of AAO nanowell surface increases due to increase of a second anodization time, the resulting sensitivity will increase because the relative contribution from resistance change of Pd nanoparticles increases. This is clearly demonstrated in FIG. 4. However, there is a practical limit, when resistance of the substrate becomes near insulating, the overall resistance of the sensor increases tremendously and the sensitivity will decrease.

We have successfully fabricated a series of Pd hydrogen sensors with a nanostructure based preferably on AAO nanowell (pores) substrates. The response times for the novel hydrogen detectors are between a few hundred milliseconds and a few seconds with good sensitivity (as defined herein) for hydrogen concentrations between 0.05% and 1%. The inventive sensors also show a moderate response for hydrogen concentrations as low as 5 ppm. The AAO nanowell or porous structure proves to be an excellent medium for Pd based hydrogen sensor that functions at room temperature.

While the invention has been particularly shown and described with reference to a preferred embodiment hereof, it will be understood by those skilled in the art that several changes in form and detail may be made without departing from the spirit and scope of the invention.

The embodiment of the invention in which an exclusive property or privilege is claimed are defined as follows:

1. A hydrogen detector comprising a substrate with a porous layer of alumina, said porous layer having pores therein with average pore diameters in the range of from about 10 to about 200 nanometers (nms) and average pore depths in the range of from about 10 to about 1000 nms, Pd nanoparticles in at least most of said pores forming a film on said alumina porous layer, and electrodes in electrical contact with said Pd film for measuring changes in electrical resistance of said Pd film in the presence of hydrogen.

2. The hydrogen detector of claim 1, wherein said average pore diameters are in the range of from about 30 to about 100 nms.

3. The hydrogen detector of claim 1, wherein said average pore diameters are not less than about 40 nms.

4. The hydrogen detector of claim 1, wherein said average pore depth is not less than about five times said average pore diameter.

5. The hydrogen detector of claim 4, wherein said nanoparticles are at least mostly nanotubes.

6. The hydrogen detector of claim 1, wherein said Pd film has a root means square (RMS) surface roughness greater than about 4 nms.

7. The hydrogen detector of claim 1, wherein said substrate is Al.

8. The hydrogen detector of claim 1, wherein the detector sensitivity is greater than 1 when the hydrogen concentration is 0.2% by volume.

9. The hydrogen detector of claim 1, wherein the detector sensitivity is greater than 2 when the hydrogen concentration is 0.4% by volume.

10. The hydrogen detector of claim 1, wherein said substrate is electrically weakly conductive.

11. The hydrogen detector of claim 1, wherein said Pd nanoparticles have average widths of about 10 nm and average thickness of about 2 nms.

12. A hydrogen detector comprising a substrate with a layer of alumina having pores therein oriented in a hexagonally close packed configuration, said pores having average pore diameters in the range of from about 10 to about 200 nanometers (nms) and average pore depths in the range of from about 50 to about 1000 nms with said average pore depth being at least five times said average pore diameter, Pd nanotubes in at least most of said pores forming a film on said alumina layer, and at least two electrodes in electrical contact with said Pd film for measuring changes in electrical resistance of said Pd film in the presence of hydrogen.

13. The hydrogen detector of claim 12, wherein said substrate is aluminum foil.

14. The hydrogen detector of claim 13, wherein the average diameter of said pores is in the range of from about 30 to about 100 nms.

15. The hydrogen detector of claim 14, wherein the average pore depth is in the range of from about 150 to about 1000 nms.

16. The hydrogen detector of claim 12, wherein the detector sensitivity is greater than 1 when the hydrogen concentration is 0.2% by volume.

17. The hydrogen detector of claim 12, wherein the detector sensitivity is greater than 2 when the hydrogen concentration is 0.4% by volume.

18. The hydrogen detector of claim 12, wherein said substrate is electrically weakly conductive.

19. The hydrogen detector of claim 12, wherein said Pd nanotubes have a RMS surface roughness greater than about 4 nms.

20. A method of providing a layered combination useful in detecting the presence of hydrogen, comprising the steps of: (a) providing an aluminum substrate having nanoindents on at least one surface thereof, (b) anodizing the surface having the nanoindents therein for a time sufficient to form pores having average diameters in the range of from about 10 to about 200 nms and average pore depths in the range of from about 10 to about 1000 nms, and (c) providing Pd nanoparticles in at least most of the pores forming a Pd film on the anodized surface.

* * * * *